United States Patent [19]
Jeris

[11] 4,182,675
[45] Jan. 8, 1980

[54] WASTE TREATMENT PROCESS

[75] Inventor: John S. Jeris, Yonkers, N.Y.

[73] Assignee: Ecolotrol, Inc., Bethpage, N.Y.

[21] Appl. No.: 917,162

[22] Filed: Jun. 20, 1978

Related U.S. Application Data

[63] Continuation of Ser. No. 738,867, Nov. 4, 1976, abandoned, which is a continuation of Ser. No. 633,153, Nov. 18, 1975, abandoned, which is a continuation of Ser. No. 487,974, Jul. 12, 1974, abandoned.

[51] Int. Cl.² .............................................. C02C 1/04
[52] U.S. Cl. ......................................... 210/8; 210/20
[58] Field of Search ................... 210/2, 16, 17, 20, 11, 210/14, 269, 275, DIG. 28, 276, 279; 48/197 A

[56] References Cited

U.S. PATENT DOCUMENTS

| | | | |
|---|---|---|---|
| 3,640,846 | 2/1972 | Johnson | 210/2 |
| 3,846,289 | 11/1974 | Jeris | 210/11 |

OTHER PUBLICATIONS

Lawrence, A. W., "Application of Process Kinetics to Design Anaerobic Processes" Found in Anaerobic Biological Treatment Processes; A.C.S. (1971).

Jennet, J. C. et al.; "Anaerobic Filter Treatment of Pharmaceutical Waste"; Jour. W.P.C.F., vol. 47, No. 1 (Jan. 1975).

*Primary Examiner*—Benoit Castel

[57] ABSTRACT

A biological process for removing biochemical oxygen demand from waste water by forming a fluidized bed of microorganisms attached to a solid particulate carrier, continuously passing waste water to be treated through said fluidized bed, retaining the waste water in the fluidized bed for a sufficient period of time while controlling other necessary parameters to biologically convert substantially all of the biochemical oxygen demand to be removed from the waste water to methane gas, carbon dioxide and cellular material, and thence withdrawing the biologically converted products. In one form of the invention nitrified effluent is added to the waste water and the mixture is biologically converted to methane gas, carbon dioxide, nitrogen gas and cellular material.

11 Claims, 2 Drawing Figures

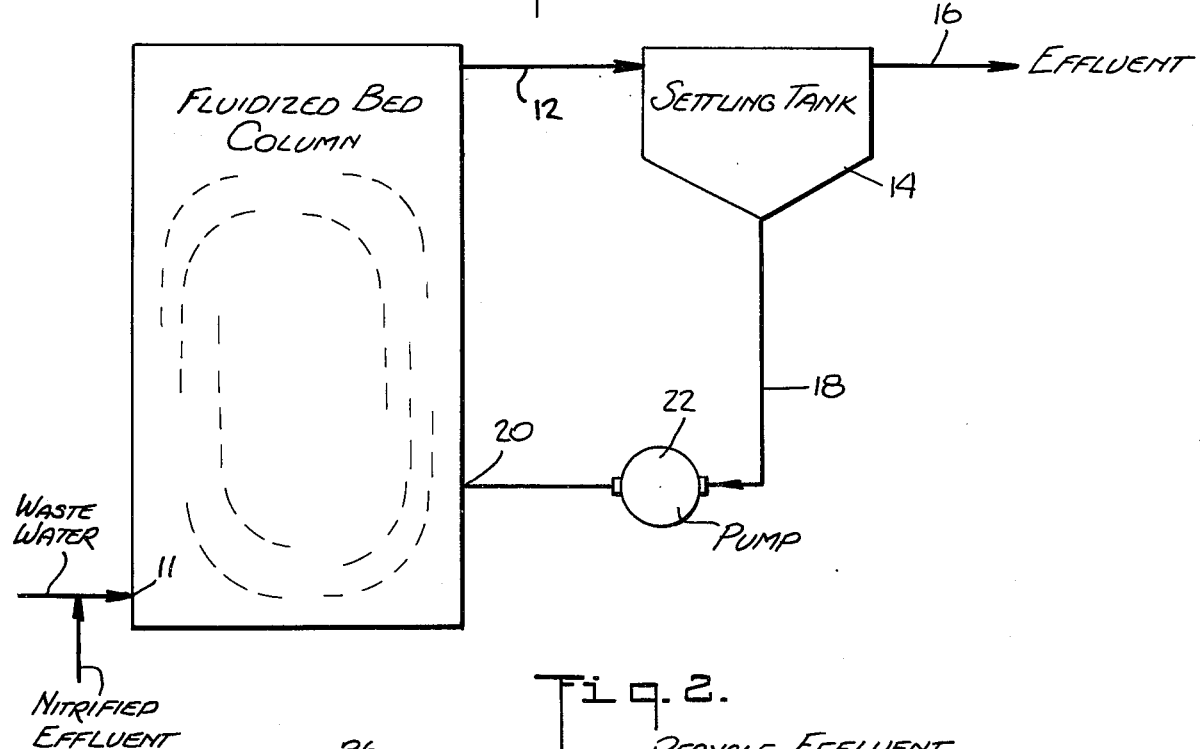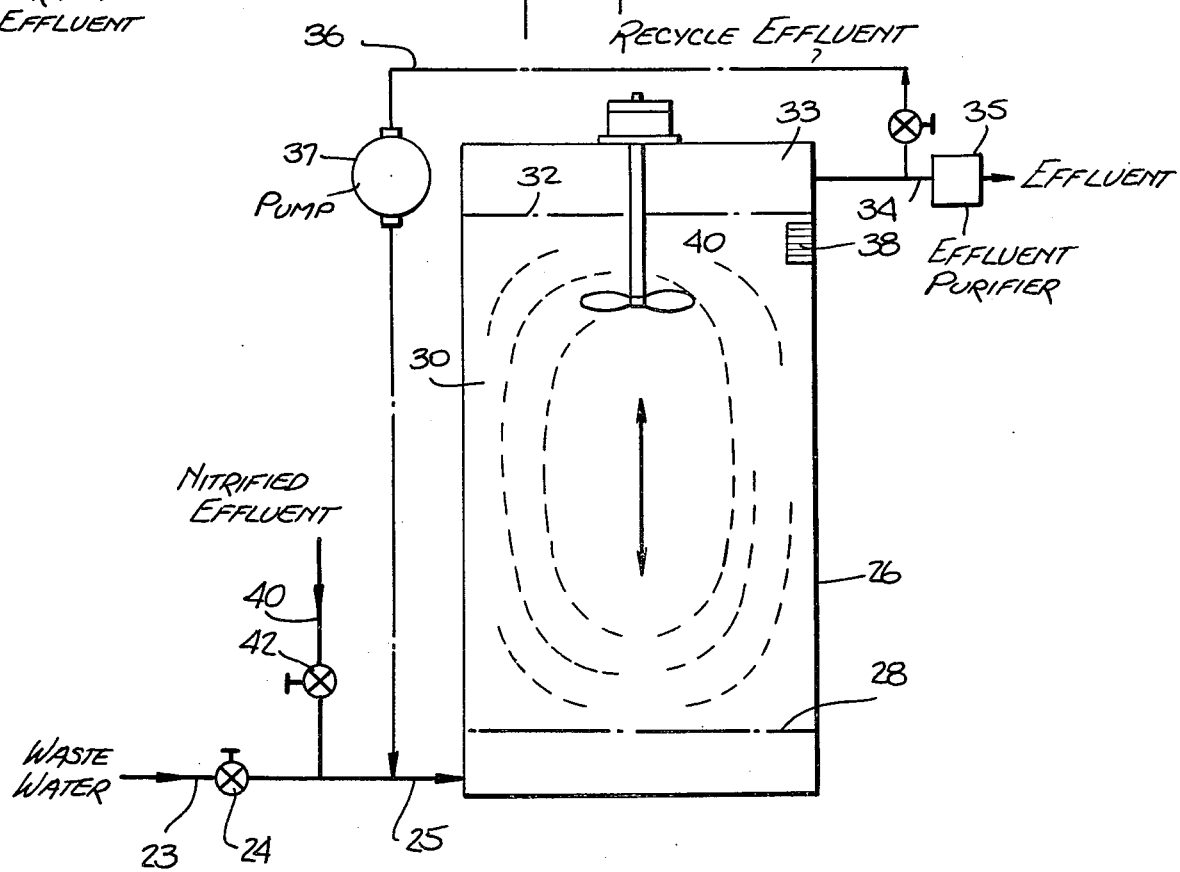

WASTE TREATMENT PROCESS

This is a continuation of application Ser. No. 738,867, filed Nov. 4, 1976, which is a continuation of Ser. No. 633,153, filed Nov. 18, 1975, which is a continuation of Ser. No. 487,974, filed July 12, 1974, all now abandoned.

BACKGROUND OF THE INVENTION

The invention relates to apparatus and process for the biological treatment of liquid wastes employing fluidized beds. In particular, it is directed to a process for removing organic carbon or biochemical oxygen demand from waste water, and in one form it also removes oxidized nitrogen from nitrified effluent.

Waste water treatment plants are typically designed to remove solids and oxygen demanding organic material. Traditionally, activated sludge or trickling filter processes were employed to accomplish the required treatment incorporating theuse of primary and final settling tanks for solids removal. Activated sludge treatment involves the use of microbial organisms to consume the organic wastes. The organisms are cultured as suspended solids in biologically active aeration tanks. Biological oxidation is accomplished primarily in the aeration tank where from 1000 to 4000 mg/l of highly active biological solids are typically maintained under aerobic conditions. Air is most often used to provide sufficient oxygen for the oxidative process as well as to keep the waste liquor well mixed with the suspended solids to prevent settling in the aeration tank. In conventional activated sludge treatment systems, about six hours of aeration time is required to provide satisfactory removal of the organic contaminants. Following the aeration step the waste liquor with the suspended solids are conveyed into the final setting tank where the supernatant liquor is separated from the suspended solids, the liquor is normally discharged as the final effluent, while the suspended solids are partially wasted and recycled to the aeration tank where they again consume organic waste.

Traditional trickling filter processes employ four to ten foot beds of 2 to 4 inch stone, upon which biological slimes grow. Liquid waste is intermittently applied over the stones, typically by a rotary distributor which revolves around the circular trickling filter bed of stones. As waste water trickles over the biological slimes covering the stones, the organic wastes are oxidized. Air which fills the voids of the stones provides the oxygen necessary for the biological oxidation.

Both the traditional activated sludge and trickling filter processes are costly and require much space and extensive building requirements. Construction costs of the two processes are fairly comparable in small sized plants, but activated sludge is often more economical for larger installations. In general, those processes provide a substantial reduction of the five-day biochemical oxygen demand $(EOD)_5$ and suspended solids present in, for example, municipal waste water. These processes, in effect, convert the organic contaminant, typically measured as $BOD_5$, to innocuous carbon dioxide and water; but also produce biological mass which must be given further treatment. Such processes are highly expensive and require much land, personnel and lead time to design and construct to meet today's critical needs for waste water purification systems.

New activated sludge processes in the developmental stages use pure oxygen and suspended solids of 3,000 to 6,000 mg/l in the aeration tanks, but still require from 2 to 4 hours aeration time, as well as bulky tanks and piping systems.

In the past, experimenters have employed up-flow expanded beds containing activated carbon for the absorption of minor amounts of organic carbon (BOD) that remained after conventional biological treatment or physical/chemical treatment. Such absorption processes employing expanded beds were primarily experimental and not used for large scale waste water purification systems. Frequent back-washing or regeneration of the system was needed as the pores in the activated carbon tended to become rapidly filled with contaminants. Examples of such up-flow expanded bed type systems are described in the following publications: Weber, W. J. Jr., Hopkins, C. B. and Bloom, R. Jr. "Physiochemical Treatment of Waste Water", Journal of Water Pollution Control Federation, 42, 83–89 (1969); Weber, W. J. Jr., Hopkins, C. B. and Bloom R. Jr., "Expanded-Bed Active-Carbon Adsorption Systems for Waste Water Treatment", Gloyna and Eckenfelder, Ed. University of Texas Press, 1970; and in U.S. Pat. No. 3,658,697 issued Apr. 25, 1972. However, it will be particularly appreciated that the biochemical oxygen demand was primarily removed from the waste water by an adsorption process and not by a biological process. In addition, an up-flow expanded bed of activated carbon was employed as compared to a fluidized bed, as will be discussed more fully hereinafter.

Laboratory scale experimentation has been conducted using up-flow packed bed reactors operated under anaerobic conditions. These reactors used 1 to 1.5 inch stones as a media and required an 18 hour detention time to achieve 90 percent BOD removal.

While the art has recognized the desirability of employing biological organisms to remove organic carbon, it has not succeeded in providing an inexpensive and highly efficient process for rapidly treating large quantities of waste water. Accordingly, there exists a critical need for a process free of the defects and deficiencies of the prior art to purify waste water.

| U.S. Pats. | | |
|---|---|---|
| No. 2,676,919 | M. Pirnie | April, 1954 |
| No. Re 24,219 | M. Pirnie | September, 1956 |
| No. 2,834,466 | L. Hament | May, 1958 |
| No. 2,992,986 | W. T. Ingram | July, 1961 |
| No. 3,075,828 | Tsuneo Kato et al. | January, 1963 |
| No. 3,173,862 | J. S. Clements et al. | March, 1965 |
| No. 3,219,577 | T. J. Powers | November, 1965 |
| No. 3,424,674 | P. J. Webber | January, 1966 |
| No. 3,232,434 | W. Albersmeyer | February, 1966 |
| No. 3,371,033 | E. D. Simmons et al. | February, 1968 |
| No. 3,401,113 | R. D. Pruessner et al. | September, 1968 |
| No. 3,543,937 | J. M. Choun | December, 1970 |
| No. 3,547,816 | Horiguchi et al. | December, 1970 |
| No. 3,709,364 | Savage | January, 1973 |

Publications

Tamblyn, T. A. and Sword, Bryan R.; "The Anaerobic Filter for the Denitrification of Agricultural Subsurface Drainage" Paper presented at 24th Annual Purdue Industrial Waste Conference, Lafayette, Indiana on May 7, 1969.

Beer, Carl, "Evaluation of Anaerobic Denitrification

Publications

Processes", Proc. Paper 7211, Seidel, D. F. and Crites, R. W., Ed., (April, 1970).

Castaldi, F. and Jeris, J. S., "Still Wanted: Economical Controlled Denitrification", Water and Wastes Engineering Vol. 41, 36-38 (June, 1971).

Beer, C., Jeris, J.S. and Mueller, J. A. "Biological Denitrification of Effluents in a Fluidized Granular Bed, Phase I" prepared for N.Y. State Department of Environment Conservation, publ. Manhattan College; (March, 1972).

Weber, W. J. Jr., and Morris, J. C. "Kinetics of Adsorption in Columns of Fluidized Media", Journal of American Water Works Association, pp. 425, 430, Vol. 443, (1965).

St. Amant, P. P. and McCarty P. L., "Treatment of High Nitrate Waters", Journal of American Water Works Association pp. 659-662, (1969).

McCarty, Perry L. and Haug, Roger T., "Nitrification with submerged Filters" Journal Water Pollution Control Federation, Vol. 44, No. 11 (November, 1972).

McCarty, Perry L. and Young, James C., "The Anaerobic Filter for Waste Treatment", Journal Water Pollution Control Federation, Vol. 41, R160 (1969).

Weber, W. J., Jr., Friedman, L. D. and Bloom, R. Jr., "Biologically - Extended Physicoclogical Treatment", Paper presented at 6th International Water Pollution Control Conference at the University of Michigan on June 22, 1972.

SUMMARY OF THE INVENTION

It is, therefore a primary object of the invention to provide a relatively inexpensive process employing biological organisms for reducing the biochemical oxygen demand of waste water.

As employed in the application the term "waste water" or "liquid waste" includes organic or inorganic liquids or mixtures thereof containing biologically decomposable contaminants. Preferably, the waste water to be processed contains the equivalent of at least about 50 milligrams per liter of biochemical oxygen demand (BOD) particularly in the organic carbon form of BOD. Almost all municipalities and industries dealing with material have waste water which contains BOD within the above definition.

It is another object of the invention to reduce the BOD of waste water employing a fluidized bed of biological organisms and simultaneously controlling the tendency of the bed particles to become excessively enlarged by excess biological growth.

It is an additional object to treat waste water containing significant amounts of suspended solids without effectively reducing the efficiency of the process.

A further object of the invention is to provide an efficient waste treatment process adapted to operate at lower detention times compared to traditional processes.

The above and other objects are met in a process for removing organic carbon from waste water to reduce biochemical oxygen demand by generating a fluidized bed from waste water and biota adapted to reduce biochemical oxygen demand by use of anaerobic or facultative biota attached to a solid particulate carrier adapted to be fluidized; then allowing sufficient detention time in the bed for the biota to reduce the biochemical oxygen demand of the waste water passing therethrough and thereafter removing excess bacterial growth formed on said carrier during the process.

The term "fluidized bed" as employed herein refers to the flow of a suitable liquid upwardly through a bed of suitably sized particles at a velocity sufficiently high to buoy the particles, to overcome the influence of gravity, and to impart to them an appearance of movement within the bed; said bed being expanded to a greater depth than when no flow is passing therethrough. The particles travel to different parts of the bed and are imparted with movement within the bed. On the contrary, in an expanded bed as employed in the prior art systems such as the systems mentioned hereinbefore in connection with the two Weber et al publications and the Huether Pat. No. 3,658,697, the particles are primarily substantially motionless and are merely suspended in a given volume by the water passing therethrough.

As waste water containing BOD in the form of organic carbon or the like, is passed through the fluidized bed, bacterial growth on the particles is accelerated and the bed-particle size increases. If unchecked, the bed particles become enlarged and may agglomerate, thus reducing the biological surface area per unit volume of the reactor and the efficiency of the column. Further, the particles tend to be reduced in specific gavity as they enlarge and/or agglomerate and tend to be carried away from the bed. It is a feature of the present process that this excess cellular material or bacterial growth formed on the particles during the process is mechanically removed thereby overcoming the tendency of the particles to be carried away in the process effluent. Accordingly, the term "excess cellular material" as employed herein refers to the excess of such material attached to the particulate carrier beyond that needed for the normal operation of the system.

Employing a fluidized bed for biological treatment also permits waste water containing substantial amounts of suspended matter to be treated. Such suspended matter readily passes through the fluidized bed. Other types of beds, such as packed beds, are subject to plugging and excess pressure losses caused by excess growth and by retention of suspended particulate matter contained in waste water.

Another substantial advantage of the present fluidized bed process is the unexpectedly high flow rates per unit volume of reactor and removal efficiencies achieved by the fluidized system. The process is readily adapted to meet the water and waste water purification needs of municipalities and industry.

In view of the foregoing, this invention contemplates a new and improved biological process for removing biochemical oxygen demand from waste water which includes the steps of forming a fluidized bed of microorganisms attached to a solid particulate carrier, continuously passing waste water to be treated through the fluidized bed, and retaining the waste water in the fluidized bed for a sufficient period of time, while maintaining the fluidized bed at a sufficient temperature, and while maintaining the fluidized bed under anaerobic conditions to biologically convert substantially all of the biochemical oxygen demand to be removed from the waste water to methane gas, carbon dioxide and cellular material. The process further comprises the steps of continuously withdrawing the methane gas and carbon dioxide from the fluidized bed, and removing excess cellular material from the particulate carrier.

In on form of the invention nitrified effluent is added to the waste water and the mixture is biologically converted to methane gas, carbon dioxide, nitrogen gas and cellular material. In another form of the invention apparatus is provided to effect the foregoing process.

BRIEF DESCRIPTION OF THE DRAWINGS

FIG. 1 is a flow sheet illustrative of the process of the invention with the various processing components shown more or less diagrammatically, and FIG. 2 is a flow sheet illustrative of the process of a second embodiment of the invention.

DESCRIPTION OF THE PREFERRED EMBODIMENTS

While applicable to the treatment of any fluid containing BOD to which bacteria can become acclimated, the present process is most readily adapted to augment or supplant secondary waste water treatment systems. Designed for secondary treatment of waste water, the process may also be installed at overloaded conventional trickling filter plants or activated sludge processing facilities, particularly where land availability is limited.

For most practical applications, the waste water to be treated will contain at least the equivalent of about 50 milligrams per liter of Biochemical Oxygen Demand. Of course, the process is able to treat waste water containing less than this amount. The process is also readily adapted to treat conventional sewage containing upwards of 200 milligrams per liter of BOD.

There is no need for any external additions of material such as $O_2$ to the waste water in carrying out the process. Besides removing BOD from the waste water, the process will also remove nitrates, nitrites or other oxidized contaminants. The effluent from a nitrification process could then be mixed with the influent waste water to remove the nitrates or nitrites. This would reduce the amount of denitrification required when necessary at the installation.

By way of an example of the process, waste water is passed through the up-flow fluidized bed according to the invention in the presence of appropriate microorganisms which convert organic carbon and/or BOD into methane gas, carbon dioxide and cellular material. A general equation for the biological phenomenon may be expressed as follows:

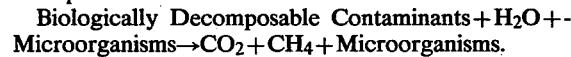
Biologically Decomposable Contaminants + $H_2O$ + Microorganisms → $CO_2$ + $CH_4$ + Microorganisms.

If effluent containing nitrites or nitrates are recycled from a nitrification process, the general equation may be expressed as follows:

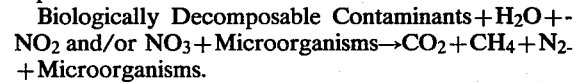
Biologically Decomposable Contaminants + $H_2O$ + $NO_2$ and/or $NO_3$ + Microorganisms → $CO_2$ + $CH_4$ + $N_2$ + Microorganisms.

The amount of nitrified effluent to be mixed with the waste water would depend on the denitrification requirements of the facility. Generally, a ratio of municipal waste water to nitrified effluent of the order of about 1:1 to about 1:3 is preferable.

A fluidized bed system is preferably generated by passing waste water through an upright cylindrical column containing microorganisms attached to a particulate carrier or substrate. In general, the carriers are seeded with bacteria or microorganisms adapted to feed on waste water such as anaerobic or facultative bacteria including the methane formers.

Suitable carrier materials for the biota or microorganisms include natural or artificial materials such as coal, volcanic cinders, glass or plastic beads, sand, alumina, garnet and activated carbon particles. The size of the particles chosen is a function of both specific gravity and surface area. For the most part, the carrier particles are between 0.2 and about 3 millimeters in diameter. Employing the preferred flow rates of the present invention, enhanced results are obtained by bed particles having a diameter of from about 0.4 to about 1.5 millimeters. The above discussion assumes the presence of spherical particles, but the carrier particles in most cases would not be spherical. Most preferably, the particles are of a uniform size. It will be appreciated that other materials, nontoxic to the micro-organisms, whether natural or synthetic, can be employed.

For enhanced biochemical oxygen demand removal, the bed particles preferably have a thin layer of bacteria seeded thereon. Preferably, the bed particles are first cultured with seed bacteria such as those present in sewage. Seeding is provided externally, or preferably, internally within the fluidized bed column. For this purpose the carrier particles are introduced into the column and thereafter waste water which is to be treated is fed through the column. It has been found that seeding is enhanced by recycling all or a portion of the flow, and controlling the pH and concentration of the BOD. Seed bacterial or bacterial naturally present in the sewage rapidly grow around the bed particles and become acclimated to the system. The specific gravity of the seeded particles is preferably no less than 1.1 and preferably at least about 1.2 in order to insure that seed particles are not carried out of the system during operation of the fluidized bed.

By way of an example of the operation, waste water enters a vertical cylindrical column through a distribution manifold in the column base. A suitable distribution manifold has a series of spaced apart inlet ports which regulate the flow of waste water through the column. Obviously, a wide assortment of conventional distribution manifold systems could also be utilized.

The pressure of the waste water influent at the point of fluidization varies depending on many factors, including the quantity of bed particles and their specific gravity and the degree of pressurization set in the column. For the vertical column fluidized bed systems, the feed is pumped into the column at a rate sufficient to support the seeded particles in the state of fluidization as hereinbefore described.

In general the flow rate into the column is sufficient to provide a fluidized bed according to the invention. Depending upon the size and specific gravity of the bed particles, among other factors, the flow rate is usually at least about 6 gallons per minute per square foot of bed. By adjusting the specific gravity of the bed particles, by employing denser bed particles and the like the process can be carried out at very high flow rates, possibly even of the order of hundreds of gallons per minute per square foot of bed. Commercially, it is desirable to operate at flow rates approaching 100 gallons per minute per square foot of bed. Fluidized beds operating according to the fundamental principles of the present invention have been successfully operated at flow rates of about 25 gallons per minute per square foot of bed and operations at higher rates are well within present technology as set forth herein.

It has been found that enhanced results are obtained, and, accordingly, it is preferred to provide a flow rate into the column from about 6 to about 40 gallons per minute per square foot of natural or artifical bed. Further enhanced results are obtained when the flow rate is from about 8 to 25 gallons per minute per square foot of bed. Depending upon the specific flow rate selected, the actual dwell time within the column for a volume of waste water can be as little as from about 2 to about 5 minutes. In general, the dwell time within the column is usually under about 30 minutes and most frequently less than about 15 minutes for up to about 12 feet of bed height, but the actual dwell time is a function of the size of the reactor. The flow rate is preferably adjusted to compensate for the size and specific gravity of the seed particles.

For a given bed, as the flow rate is increased in order to increase the volume of waste water being treated, the specific bed of microorganism attached particles will increase in height. In order to compensate for the tendency of the bed to increase in height at higher flow rates, it is desirable to employ additional bed particles or to employ bed particles of higher specific gravity.

As the waste water is pumped into the column an area immediately above the distribution manifold may be free of seeded particles although bed particles with sufficient growth may remain. This phenomenon has also been observed during the initial seeding periods of the bed but disappeared as seeding the carrier particles progressed. This interface height, then, (the height from the distribution manifold to the bottom of the seeded fluidized bed in a vertical column) is a function of the flow rate of the column, the temperature, the specific gravity of the bed particles and the length of time of the seeding period as well as the nature of the distribution manifold. Practically, this phenomenon has a minimal effect, if any, on the column's efficiency. Generally as flow rate increases interface height increases and conversely as flow rate decreases interface height decreases.

In general, the pH of the fluidized system will not require external manipulation. If need be, it may be adjusted to fall within the range of from about 6.4 to about 7.8. Best results are obtained at a pH from about 6.6 to about 7.4. The internal temperature of the fluidized column should be sufficient to permit bacterial activity. For this purpose the bed temperature is from about 5° to about 45° C. The bed temperature will vary with that of the influent waste water and, accordingly, ambient operating temperature on the order of from about 15° to about 30° C. will be the nominal bed temperatures and are entirely satisfactory.

As the carbon oxidation-reduction reactions and BOD removal proceeds in the fluidized bed, bacteria tend to grow on the surface of the carrier particles. After a time, if unchecked, bed particles tend to form thick layers and expand to the extent that they form agglomerates, and/or gelatinous masses. Should this be permitted to occur, then the surface area available per unit of reactor volume for biological reaction is greatly reduced and the efficiency of the process is correspondingly reduced. Further, particles tend to be carried out of the fluidized bed as their specific gravity decreases. They also tend to entrap or become attached to gas bubbles, such as those from the carbon dioxide or methane gas liberated by the reactions. The gas bubbles reduce the specific gravity of the particles and tend to carry them away from the bed toward the top of the column where they can collect as an undesirable floc and/or leave the system.

In order to overcome these problems excess bacterial growth is preferably mechanically removed from the particles although chemical and biological means or combinations thereof may be employed as supplements. Sufficient growth in the form of a thin layer of bacteria must remain on the particles in order to preserve the efficiency of the process. Removing all growth, which has been suggested in the prior art for up-flow expanded bed processes used for treating waste water to remove carbon by adsorption, destroys the efficiency of the present process. In one embodiment growth is regulated by removing predetermined quantities of bed particles from the column by a valve-controlled outlet port and mechanically agitating and abrading the particles. This operation may be performed in a separate abrasion vessel employing a mixer which resembles the rotating knife in a Waring Blender. The abraded particles are then returned to the bottom of the fluidized bed. Alternately, the particles in the abrasion vessel are subjected to the action of compressed air or water sprays to remove excess microorganisms. Other suitable agitation mechanisms and apparatus will be apparent to those skilled in the art. After treatment, the abraded particles are metered into the fluidized bed at its base by a suitable inlet port. The withdrawal of measured amounts of bed particles, their cleaning and recycling into the process can be accomplished without significant interference with the continuity of the process.

By way of example, in a second embodiment, bed particles are allowed to be carried out in the effluent from the column into a settling tank from which they are pumped into the bottom of the column. Separation of the excess cellular material growth from the particulate carrier is effected by the pump. FIG. 1 illustrates this process. Waste water and nitrified effluent are introduced into a fluidized bed column 10 through an inlet port 11 for treatment therein. Treated waste water containing bed particles is exhausted as at 12 from a fluidized bed column 10 into a settling tank 14. Separation of the treated waste water or effluent 16 and bed particles 18 occurs in the settling tank. The separated bed particles are then pumped back into the fluidized bed column as indicated at 20. Separation of the growth or excess cellular material from the carrier particles occurs by abrasion in a pump 22. When the mixture of the abraded carrier and the growth or excess cellular material is pumped back into the column 10, the carrier particles will remain in the column while the excess cellular material will be carried on through the system to the effluent 16.

By way of example, in a third and more preferred embodiment, the particles are treated in situ in order to remove excess bacterial growth from their outer surfaces. It has been found that excess bacterial growth is readily removed from floc, agglomerates and/or bed particles at the top (or downstream side) of the bed, by a sharp rotating blade or flexible agitator. These mechanisms shear the bacteria from the carrier particle and thereby remove excess growth. The stirrer provides continuous control of the height of the fluidized bed. Other mechanical mixers, baffle plates and other abrasion-type surfaces, ultrasonic reans or even water or compressed air jets directed upwardly and sidewardly against the column walls to create agitation vortices and the like, as well as other suitable conventional agitating means, can be employed within the column.

Where bacteria are abraded batchwise to control growth, it has been found that sufficient growth is removed, when the height of the fluidized bed after treatment is reduced on the order of from about 10 to about 25 percent of its original expanded length at the same flow rate. At highly elevated or substantially reduced flow rates, the height may be somewhat above or below the aforesaid range. For removal of excess growth in situ using the air cleaning method, for example, the flow rate to the column may be reduced to about ⅓ normal flow (reduction is dependent on operating flow rate). The bed will settle to a new lower height. Air is injected into the bed to cause abrasion. During and immediately after this abrasion, the removed growth is carried out of the reactor and exhausted from the system. Thereafter, the flow rate may be increased to its normal velocity.

Depending upon the nature of the waste water and the concentration of contaminants, it may prove useful to employ more than one column connected in series. It has been found practical in many cases to employ the effluent from the first column as the influent feed for a second column. Accordingly, a plural column system may provide enhanced results for treatment of municipal, industrial or other waste waters. In a two column system, BOD is further reduced by directing the effluent from the first column into the second column as the sole influent, or in combination with fresh sewage. During start-up of the column it has, in certain cases, been found useful to recycle at least a portion of the effluent treated to the column in order to promote initial growth of bacteria on the bed carrier particles in situ.

By way of example, FIG. 2 shows a somewhat preferred embodiment of the process according to the invention. Waste water is introduced through an inlet pipe 23, valve 24 and inlet port 25, into the lower portion of cylindrical column 26 through a manifold 28 in the base of the column. Microorganisms or biota-seeded bed particles are fluidized by the passage of waste water through the column and form a fluidized bed 30. The interface height of the fluidized bed is indicated at 32 forming a chamber 33 thereabove in the column. Treated waste water or effluent is exhausted from the column after passage through the fluidized bed and chamber 33, as at 34. Then the effluent may be passed through an effluent purifier 35, such as a settling tank or other treatment system, if necessary. Selected portions of the effluent, as required, are recycled through pipe line 36, containing a pump 37, to the influent waste water feed port 25. This serves the following purposes: (1) to promote growth of the biota or microorganisms on the particles during seeding operations; (2) to maintain uniform flow where input flow decreases; (3) to dilute the concentration of BOD in the bed, if necessary to provide uniform concentration of waste water; and/or (4) to permit additional removal of BOD remaining in the effluent. In one form of the invention, nitrified effluent is introduced through an inlet pipe 40, valve 42 and inlet port 25 where it is mixed with the waste water and thence the mixture is processed in the fluidized bed to biologically convert substantially all of the biochemical oxygen demand and nitrates and nitrites to be removed from the mixture to methane gas, carbon dioxide, nitrogen gas and cellular material, as aforesaid.

It is recognized, of course, that the nitrified feed includes nitrates and/or nitrites. It is within the scope of the present invention to convert nitrates to nitrites in a first column and thereafter, if desired, to convert nitrites to nitrogen gas in a second column or in a second section of the first column. It is recognized that $NO_3^-$ may be converted initially to $NO_2^-$ which is then converted to $N_2$ gas. Clearly, the process can be employed to selectively convert $NO_2^-$ in a feed to $N_2$ gas. The present process can be employed in conjunction with the nitrification fluidized bed system as set forth in my copending applicatica filed simultaneously herewith entitled "Apparatus and Process for Removing Ammonia Nitrogen from Waste Water".

During treatment, bacterial growth on the particles is monitored as a function of bed expansion by a conventional optical device or other type of solids sensor 38. When bed expansion reaches a predetermined height where the sensor device is activated, the bed particles are regenerated by abrasion or the like to remove excess growth of the cellular material. A mechanical stirrer assembly 40 is preferably provided at the top of the column to remove excess growth. The stirrer is in the form of sharp rotating blades or is formed from a flexible length of polymeric material, such as polyethylene tubing, as desired.

In some installations it is desirable to employ an upwardly, outwardly directed conical portion at the upper end of the fluidized bed column to reduce the upward flow velocity to prevent the bed particles from being carried off in the effluent, among other desirable features. Further, this feature serves at least as an assisting means for controlling the growth on the bed particles.

In some installations, the present process can be employed as the influent, or otherwise utilized in cooperation with the aerobic BOD removal process set forth in U.S. patent application Ser. No. 333,394 filed Feb. 16, 1973, cited hereinbefore.

It will be apparent that substantial amounts of BOD can be anaerobically removed in a fraction of the bed, sometimes in the first few feet adjacent the influent feed. Accordingly, aerobic conditions may be applied in a portion of the bed for enhanced operation. Also, it is evident that when the wastewater contains dissolved oxygen, the upstream portion of the bed will strip the dissolved oxygen from the system and provide anaerobic conditions at the downstream portion, sufficient to carry out the present process. Therefore, it is within the scope of the invention to include in the term "anaerobic conditions" maintaining the bed anaerobically for less than the total height of the bed.

The presently preferred embodiments of the invention have been described for purposes of explanation. It should be understood that modifications may be made therein as will appear evident to those skilled in the art to which the invention pertains. It is therefore, intended to encompass all such changes as fall within the true spirit of the invention.

What is claimed is:

1. A biological process for removing biochemical oxygen demand from waste water, which comprises:
    forming a fluidized bed of acid forming, including methane forming, microorganisms attached to a solid particulate carrier,
    continuously passing waste water consisting essentially of biochemical oxygen demand to be treated through said fluidized bed,
    retaining said waste water in said fluidized bed for a sufficient period of time while maintaining said fluidized bed at a sufficient temperature and while maintaining said fluidized bed under substantially anaerobic conditions to biologically convert substantially all of the biochemical oxygen demand to be removed from the waste water to methane gas, carbon dioxide and cellular material; and continuously withdrawing said methane gas and carbon dioxide from said fluidized bed, and removing excess cellular material from said particulate carrier to leave a thin layer of said microorganisms on said particulate carrier.

2. A biological process for removing biochemical oxygen demand from waste water according to claim 1 wherein said step of removing excess of said cellular material from said particulate carrier is effected at the downstream portion of said fluidized bed by rotating a sharp blade or flexible stirrer.

3. A biological process for removing biochemical oxygen demand from waste water according to claim 1 wherein said particulate carrier is first cultured with seed bacteria externally of said fluidized bed to form said microorganisms.

4. A biological process for removing biochemical oxygen demand from waste water according to claim 1 wherein said particulate carrier is first cultured with seed bacteria internally of said fluidized bed to form said microorganisms.

5. A biological process for removing biochemical oxygen demand from waste water according to claim 1 further comprising the step of continuously recycling at least a portion of said treated waste water through said fluidized bed.

6. A biological process for removing biochemical oxygen demand from waste water according to claim 1 further comprising passing said waste water to be treated sequentially through a series of fluidized beds and biologically processing said waste water in each bed according to the steps of claim 1.

7. A biological process for removing biochemical oxygen demand from waste water according to claim 1 wherein said waste water to be processed contains at least about 50 milligrams per liter of biochemical oxygen demand and wherein the flow rate of said waste water through said fluidized bed is upwardly at least 6 gallons per minute per square foot of fluidized bed, and wherein the dwell time of said waste water in said fluidized bed is less than about 15 minutes per up to about 12 feet of bed height, and wherein said carrier has a particle diameter of from about 0.2 to about 3 millimeters and a specific gravity of at least about 1.1.

8. A biological process for removing biochemical oxygen demand from waste water according to claim 1 wherein said waste water contains at least about 50 milligrams per liter of biochemical oxygen demand and the flow rate of said waste water through said fluidized bed is upwardly between about six and about 40 gallons per minute per square foot of fluidized bed, and wherein the dwell time of said waste water in said fluidized bed is less than about 15 minutes per up to about 12 feet of bed height, and wherein said carrier has a particle diameter of from about 0.4 to about 1.5 millimeters and a specific gravity of at least about 1.4, and wherein the pH value of the fluidized bed is between about 6.4 and about 7.8 and wherein the temperature of the fluidized bed is between about 5° and about 45° centigrade.

9. A biological process for removing biochemical oxygen demand from waste water according to claim 1 wherein said particulate carrier is one of a group consisting of coal, volcanic cinders, glass, plastic beads, sand, garnet, activated carbon and alumina.

10. A biological process for removing biochemical oxygen demand from waste water according to claim 1 further comprising the steps of removing predetermined quantities of bed particles from the bed, abrading the particles to remove excess growth and recycling the abraded particles to the process.

11. The process of claim 10 wherein a mixture of abraded particles and excess growth is recycled to the process.

* * * * *